US006447549B1

(12) United States Patent
Taft

(10) Patent No.: US 6,447,549 B1
(45) Date of Patent: Sep. 10, 2002

(54) MODULAR KNEE PROSTHESIS SYSTEM

(75) Inventor: Richard J. Taft, Austin, TX (US)

(73) Assignee: Sulzer Orthopedics Inc., Austin, TX (US)

( * ) Notice: Subject to any disclaimer, the term of this patent is extended or adjusted under 35 U.S.C. 154(b) by 0 days.

(21) Appl. No.: 09/685,049

(22) Filed: Oct. 6, 2000

(51) Int. Cl.⁷ .................................................. A61F 2/38
(52) U.S. Cl. ................... 623/20.15; 623/20.14
(58) Field of Search ........................ 623/20.15, 20.14, 623/20.28, 20.24

(56) References Cited

U.S. PATENT DOCUMENTS

| 4,016,606 A | 4/1977 | Murray et al. ................ 3/1.911 |
| 4,257,129 A | 3/1981 | Volz ............................. 3/1.911 |
| 4,262,368 A | 4/1981 | Lacey ........................... 3/1.911 |
| 4,463,751 A | 8/1984 | Bledsoe ......................... 128/80 |
| 4,619,660 A | 10/1986 | Christiansen et al. .......... 623/46 |
| 4,777,941 A | 10/1988 | Borig et al. ................... 128/80 |
| 4,936,853 A | 6/1990 | Fabian et al. .................. 623/20 |
| 4,938,769 A | 7/1990 | Shaw ............................. 623/20 |
| 4,944,757 A | 7/1990 | Martinez et al. .............. 623/20 |
| 5,019,103 A | 5/1991 | Van Zile et al. .............. 623/20 |
| 5,133,758 A | 7/1992 | Hollister ....................... 623/20 |
| 5,171,283 A | 12/1992 | Pappas et al. ................ 623/20 |
| 5,194,066 A | 3/1993 | Van Zile ....................... 623/20 |
| 5,326,361 A | 7/1994 | Hollister ....................... 623/20 |
| 5,370,701 A | 12/1994 | Finn ............................. 623/20 |
| 5,489,311 A | 2/1996 | Cipolletti ..................... 623/20 |
| 5,702,466 A | 12/1997 | Pappas et al. ................ 623/20 |
| 5,728,172 A | 3/1998 | Krieger ........................ 623/44 |
| 5,776,200 A | 7/1998 | Johnson et al. ............... 623/20 |
| 5,782,921 A | 7/1998 | Colleran et al. ............... 623/20 |
| 5,782,925 A | 7/1998 | Collazo et al. ................ 623/20 |
| 5,879,391 A | 3/1999 | Slamin ......................... 623/20 |
| 5,906,644 A | 5/1999 | Powell ......................... 623/23 |
| 5,951,603 A | 9/1999 | O'Neil et al. ................. 623/20 |
| 5,954,770 A | 9/1999 | Schmotzer et al. ........... 623/20 |
| 6,004,352 A | 12/1999 | Buni ............................ 623/20 |
| 6,010,534 A | 1/2000 | O'Neil et al. ................. 623/20 |

OTHER PUBLICATIONS

Howmedica, "Modular Replacement System" Howmedica Osteonics 1997.*
Biomet, Inc, "MAXIM The Complete Knee System" Biomet Inc. 1995 Form No. Y–BMT–394/041595/M.*

* cited by examiner

Primary Examiner—Corrine McDermott
Assistant Examiner—Thomas Barrett
(74) Attorney, Agent, or Firm—Philip S. Lyren

(57) ABSTRACT

A modular knee system includes a hinged femoral component and a distal femoral component. A plurality of first stem components are selectively compatible with the hinged femoral component. A plurality of first adaptors are selectively compatible with the first stem components and the distal femoral component. A hinge component is connected to a tibial insert. The hinge component and the tibial insert are selectively compatible with the hinged femoral component and the distal femoral component. A hinged tibial component and a proximal tibial component are selectively compatible with the tibial insert. A plurality of second stem components are selectively compatible with the hinged tibial component. Alternately, a plug component is compatible with the hinged tibial component. A plurality of second adaptors are selectively compatible with the second stem components and the proximal tibial component.

22 Claims, 6 Drawing Sheets

MODULAR KNEE PROSTHESIS SYSTEM

BACKGROUND

The disclosures herein related generally to knee prostheses and more particularly to a modular knee prosthesis system.

Knee replacement systems are provided for partial and total knee replacement. Such systems are used for distal femoral repair, proximal tibia repair, and combined distal femoral/proximal tibia repair. Because of variations in bone loss, there are variations in components required in knee replacement systems. While some of the components vary, depending on surgical requirements, there are some components which are used in all or substantially all of the replacement systems. As a result, some component modularity has been introduced.

Total knee replacement may be required for a revision hinged orthopedic application, or a hinged orthopedic application, i.e. minor bone loss; a tibial orthopedic oncology-trauma application, i.e. major tibial bone loss; a femoral orthopedic oncology-trauma application, i.e. major femoral bone loss; and a distal femur-proximal tibia orthopedic oncology-trauma application, i.e. major tibial and femoral bone loss. In these applications, component requirements vary greatly. In order to meet the requirements, a substantial inventory of components is required, and at a considerable cost. Also, several instruments and implant trials are required because of the various techniques used for each orthopedic procedure.

Therefore, what is needed is a system and apparatus that provides for modularity and flexibility between orthopedic, orthopedic oncology and orthopedic trauma surgical applications.

SUMMARY

One embodiment, accordingly, provides a system and apparatus that uses the same modular components for hinged orthopedic applications, revision hinged orthopedic applications, orthopedic oncology applications and orthopedic trauma applications. To this end, a modular knee system includes a hinged femoral component and a distal femoral component. A plurality of first stem components are selectively compatible with the hinged femoral component. A plurality of first adaptors are selectively compatible with the first stem components and the distal femoral component. A hinge component is connected to a tibial insert. The hinge component and the tibial insert are selectively compatible with the hinged femoral component and the distal femoral component. A hinged tibial component and a proximal tibial component are selectively compatible with the tibial insert. A plurality of second stem components are selectively compatible with the hinged tibial component. A plurality of second adaptors are selectively compatible with the second stem components and the proximal tibial component.

A principal advantage of this embodiment is that modular components are used for several surgical applications including hinged orthopedic applications, revision hinged orthopedic applications, orthopedic oncology applications and orthopedic trauma applications, thus reducing component inventory and costs.

DETAILED DESCRIPTION

Figure 1:
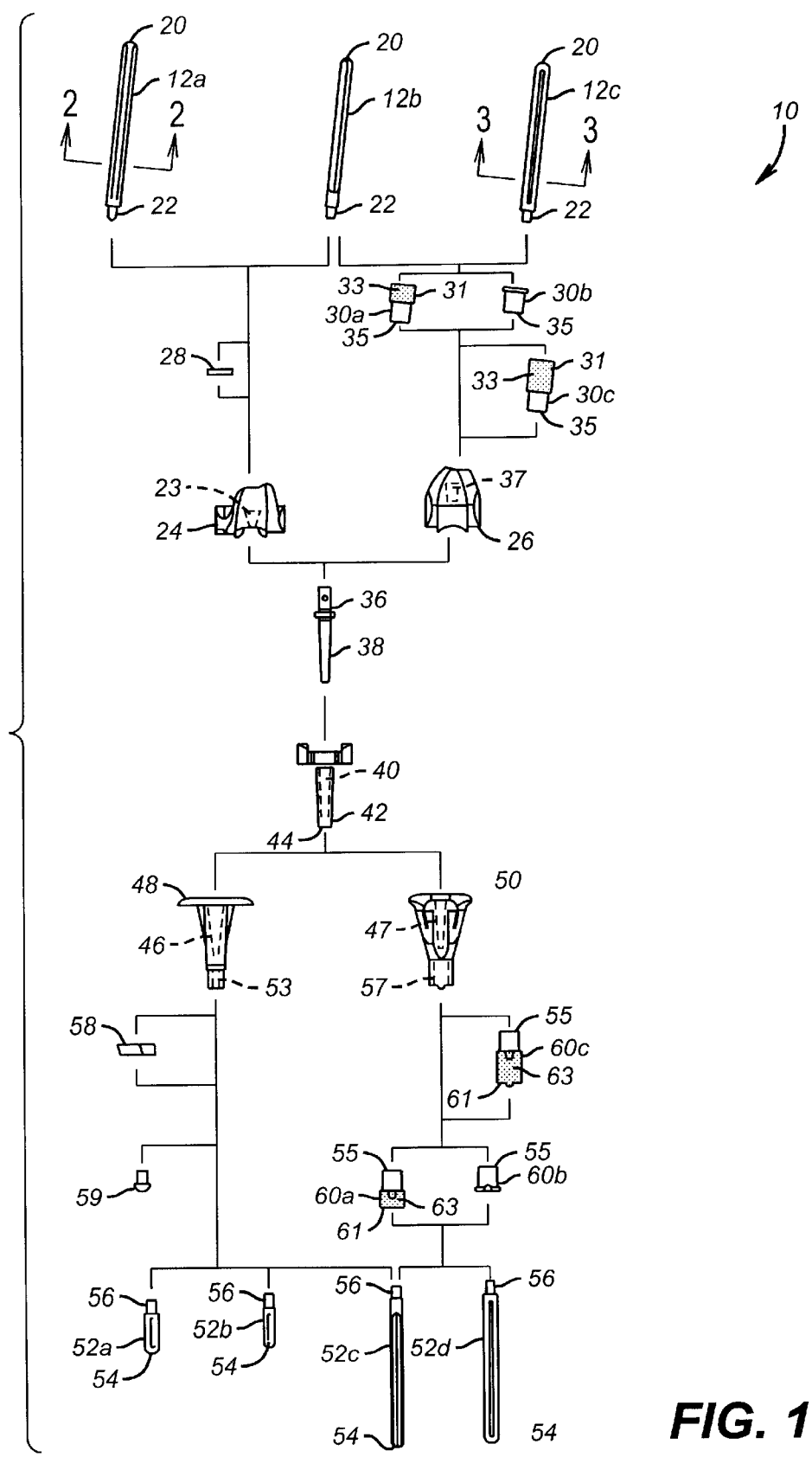
FIG. 1 is a diagrammatic view illustrating an embodiment of a modular knee prosthesis system.
Figure 2:
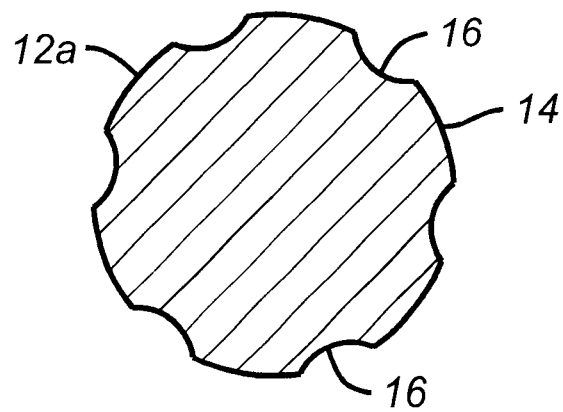
FIG. 2 is a cross-sectional view, taken along the line 2—2 of FIG. 1, illustrating an embodiment of a stem.
Figure 3:
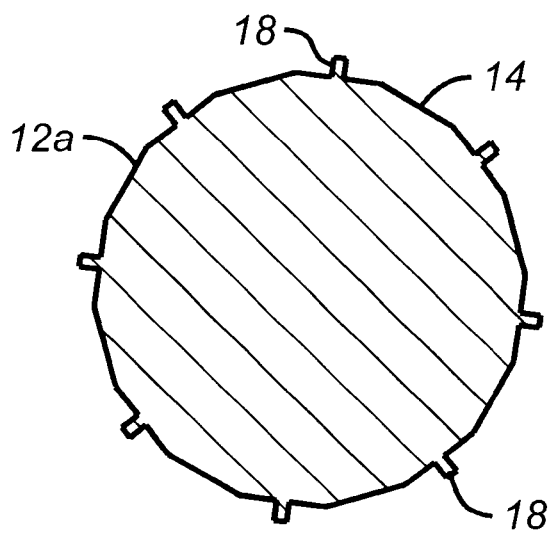
FIG. 3 is a cross-sectional view, taken along the line 3—3 of FIG. 1, illustrating another embodiment of a stem.

A modular knee system is generally designated 10 in FIG. 1. Knee system 10 includes a plurality of first stem components 12a, 12b, 12c. Stem components 12a–c may be of variable lengths, diameters and shapes as required for anatomical suitability with the intramedullary canal of a femur (not shown). The stem components 12a–c may also include a full or partial porous coating. An outer surface 14, FIG. 2, of stem component 12a may be substantially circular and include a plurality of grooves 16 extending inwardly therefrom. Alternately, the outer surface 14 of stem component 12c, FIG. 3, may be substantially circular and include a plurality of flutes 18 extending outwardly therefrom. A rounded first end 20 of each stem 12a–c inserts into the femoral intramedullary canal. A tapered second end 22 of each stem 12a–c inserts into a component discussed below.

Depending upon surgical requirements, either a hinged femoral component 24 or a distal femoral component 26 is selected. Any one of the first stem components 12a–c may be used with the hinged femoral component 24. The tapered second end 22 of the stem components 12a–c can seat in a mating tapered receptacle 23 in the component 24. A spacer or spacers 28 may be seated on the hinged femoral component 24 to provide an anatomical adjustment, if required. A plurality of first adaptors 30a and 30b, provide a selective interconnection between the tapered end 22 of the selected one of the stems 12a–c and the distal femoral component 26. The adaptor 30a is provided with an extension portion 31. The extension portion 31 may be provided with a porous coating 33 to promote bone in-growth. In addition, a segment 30c may be used in combination with the adaptors 30a and 30b. The segment 30c also has an extension portion 31 which may include the porous coating 33. Adaptors 30a and 30b, and the segment 30c, have a tapered end 35 which seats in a mating tapered receptacle 37 in the component 26.

A hinge component 36 is provided with a tapered portion 38 for insertion into a mating tapered seat 40 provided in a tibial insert 42. The hinge component 36 is connected to either the hinged femoral component 24 or the distal femoral component 26 by a known pin and bushing arrangement (not shown). The tibial insert 42 has a tapered end 44 for seating in a mating tapered seat 46, 47 in either a hinged tibial component 48 or a proximal tibial component 50, respectively. Depending on surgical requirements, either the hinged tibial component 48 or the proximal tibial component 50 is selected.

Knee system 10 includes a plurality of second stem components 52a, 52b, 52c, 52d. Stem components 52a–d may be of variable lengths, diameters and shapes as required for anatomical suitability with the intramedullary canal of a tibia (not shown). The stem components 52a–d may also include a full or partial porous coating. An outer surface of the stems 52a–d may include grooves or flutes as discussed above. A rounded first end 54 of each stem inserts into the tibial intramedullary canal (not shown). A tapered second end 56 of each stem 52a–d inserts into the hinged tibial component 48.

Any one of the second stem components 52a–d may be used with the hinged tibial component 48, or alternately, a plug 59 may be used with hinged tibial component 48. The tapered second end 56 of the stem components 52a–d, or plug 59, can seat in a mating tapered receptacle 53 in the component 48. A spacer or spacers 58 may be seated on the hinged tibial component 48 to provide an anatomical adjustment, if required. A plurality of second adaptors 60a and 60b, provide a selective interconnection between the tapered end 56 of the selected one of the stems 52a–d and the proximal tibial component 50. The adaptor 60a is provided with an extension portion 61. The extension portion 61 may be provided with a porous coating 63 to promote bone in-growth. In addition a segment 60c may be used in combination with the adaptors 60a and 60b. The segment 60c also has an extension portion 61 which may include the porous coating 63. Adaptors 60a and 60b, and the segment 60c have a tapered end 55 which seats in a mating tapered receptacle 57 of the component 50.

In operation, the hinged femoral component 24 and the distal femoral component 26 are provided. The plurality of first stem components 12a–c are provided and are compatible with the hinged femoral component 24. One of the first stem components 12a–c is selected. The plurality of first adaptors 30a and 30b are provided and are compatible with the first stem components 12a–c and the distal femoral component 26. One of the femoral components 24, 26 is selected. If the hinged femoral component 24 is selected, it is connected to the selected first stem component 12a–c. One of the first adaptors 30a, 30b is selected in the instance where the distal femoral component 26 is selected as an alternate to the hinged femoral component 24. The selected one of the first adaptors 30a, 30b is connected between the distal femoral component 26 and the selected first stem component 12a–c. The selected one of the femoral components 24, 26 is connected to the hinge component 36 which is attached to the tibial insert 42. The hinged tibial component 48 and the proximal tibial component 50 are provided. The second stem components 52a–d are compatible with the hinged tibial component 48. One of the second stem components 52a–d is selected for connection to the hinged tibial component 48, or alternately, the plug 59 is selected to be attached to the hinged tibial component 48. In the instance where the proximal tibial component 50 is selected, the second adaptors 60a and 60b are provided, and, the selected one of the second adaptors 60a, 60b, is positioned between the selected one of the second stem component 52a–d and the proximal tibial component 50.

Figure 4:
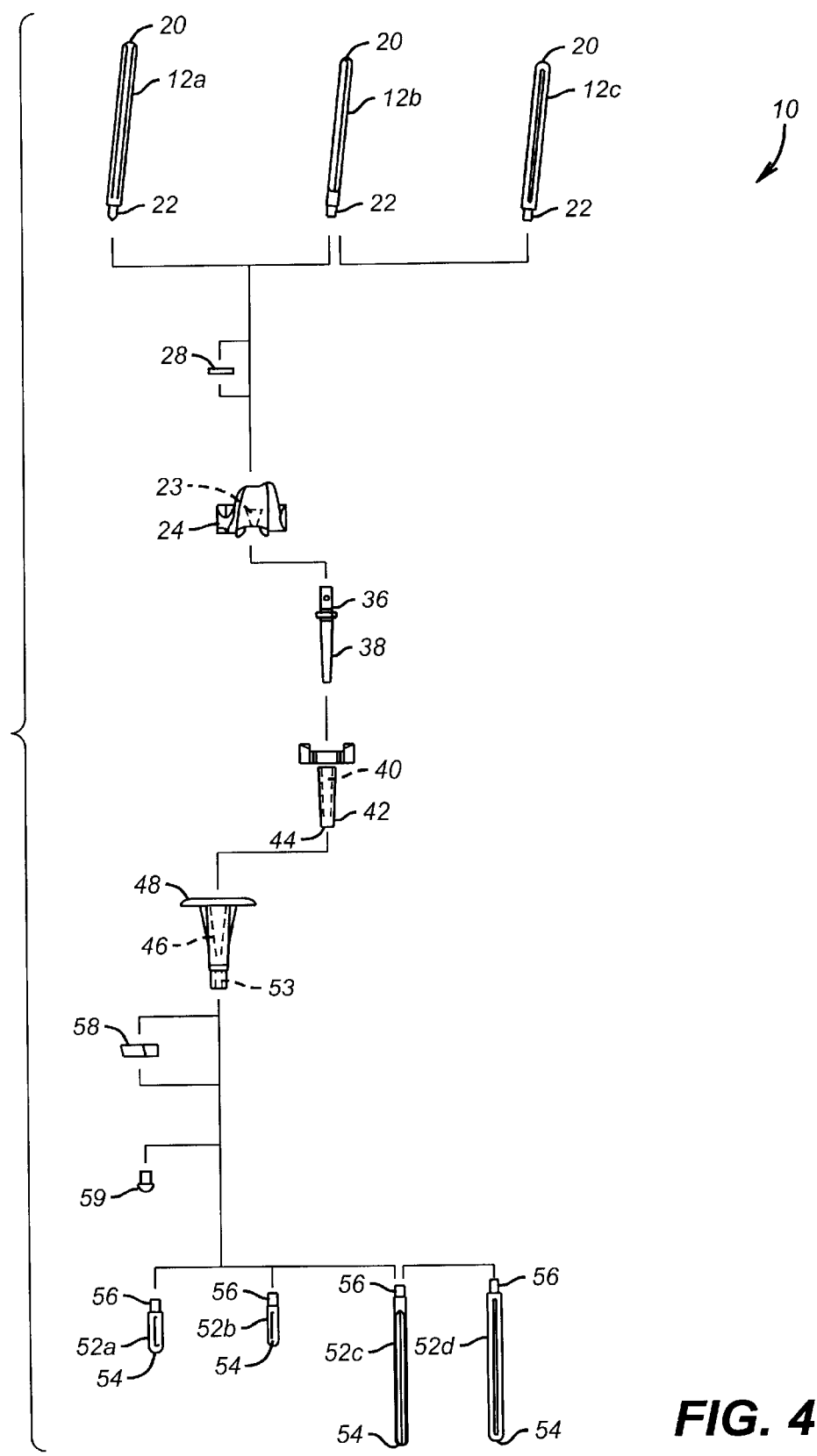
FIG. 4 is a diagrammatic view illustrating an embodiment of a hinged modular knee application.

As a result, one application for the modular system 10, is illustrated in FIG. 4. A selected one of the first stems 12a–c may be connected to the hinged femoral component 24. A selected one of the second stems 52a–d may be connected to the hinged tibial component 48, or alternately, the plug 59 may be connected to the hinged tibial component 48. The hinged femoral component 24 may be interconnected with the hinged tibial component 48 by means by the hinge component 36 and the tibial insert 42. If anatomical adjustment is required, the spacer 28 may be used with the hinged femoral component 24, and the spacer 58 may be used with the hinged tibial component 48.

Figure 5:
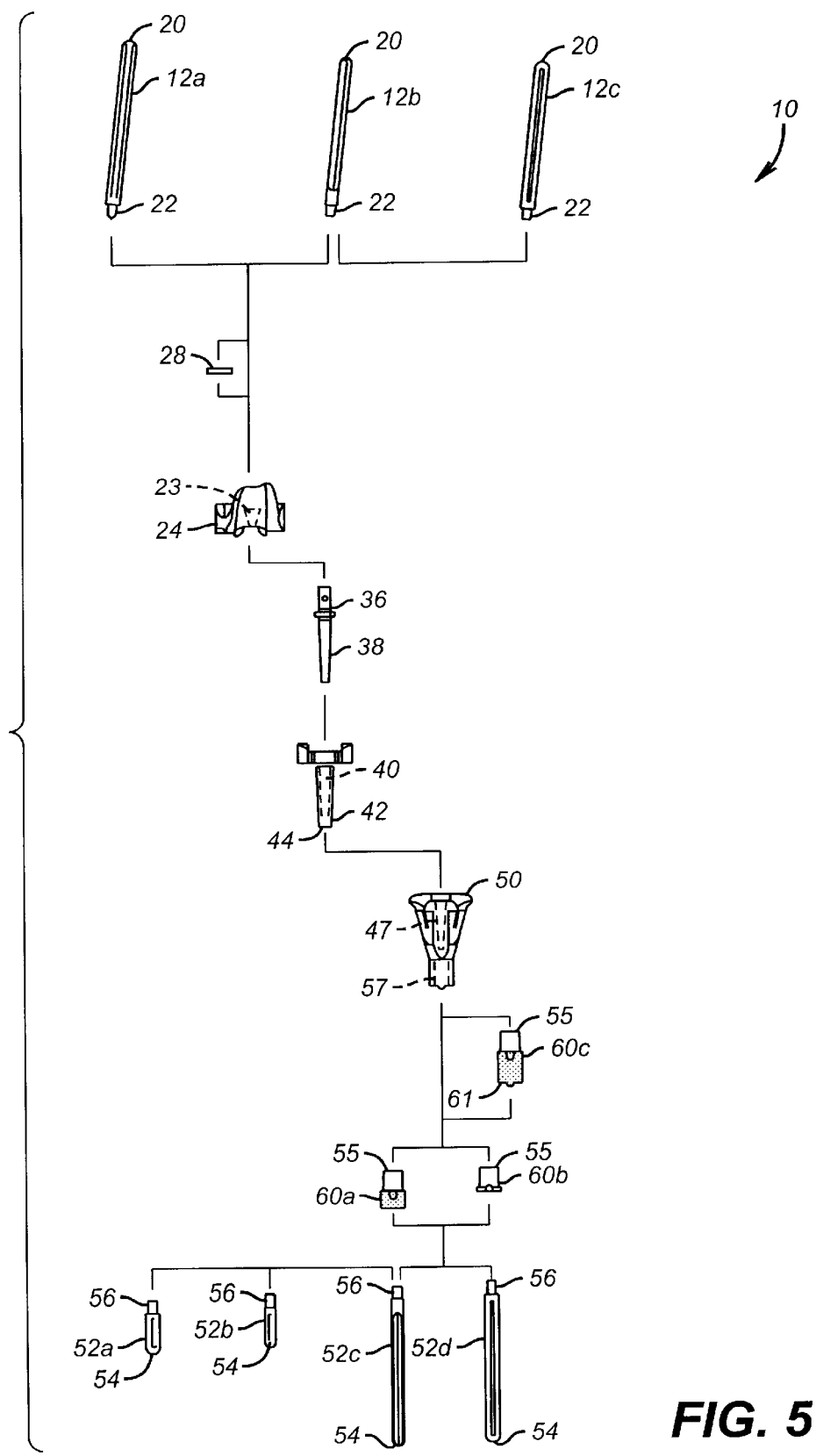
FIG. 5 is a diagrammatic view illustrating another embodiment of a hinged modular knee application.

Another application for the modular system 10 is illustrated in FIG. 5. A selected one of the first stems 12a–c may be connected to the hinged femoral component 24. A selected one of the second stems 52a–d and a selected one of the second adaptors 60a, 60b, may be connected to the proximal tibial component 50. The hinged femoral component 24 may be interconnected with the proximal tibial component 50 by means of the hinge component 36 and the tibial insert 42. If anatomical adjustment is required, the spacer 28 may be used with the hinged femoral component 24.

Figure 6:
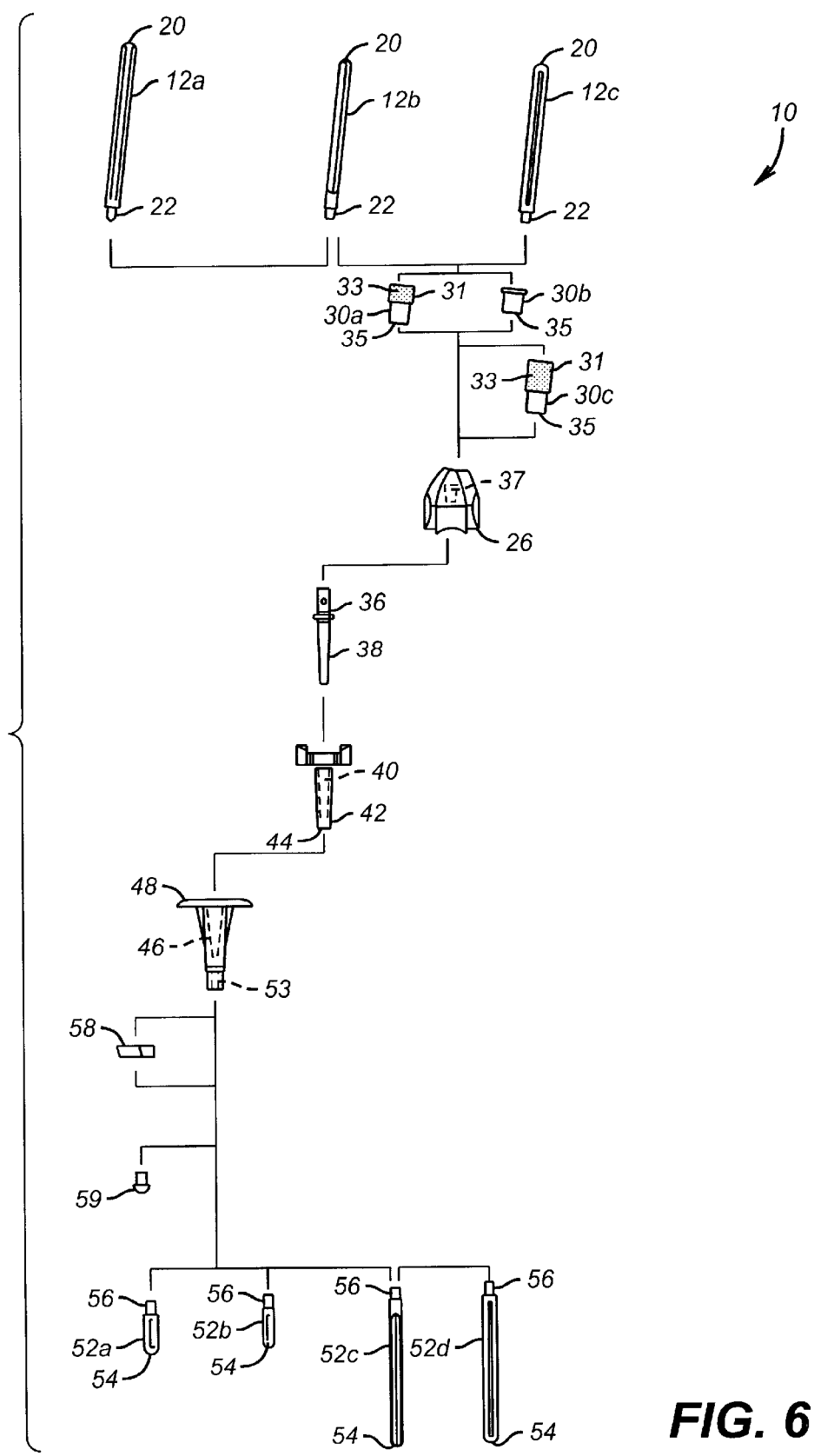
FIG. 6 is a diagrammatic view illustrating a further embodiment of a hinged modular knee application.

A further application for the modular system 10 is illustrated in FIG. 6. A selected one of the first stems 12a–c and a selected one of the first adaptors 30a, 30b, may be connected to the distal femoral component 26. A selected one of the second stems 52a–d may be connected to the hinged tibial component 48, or alternately, the plug 59 may be connected to the hinged tibial component 48. The distal femoral component 26 may be interconnected with the hinged tibial component 48 by means of the hinge component 36 and the tibial insert 42. If anatomical adjustment is required, the spacer 58 may be used with the hinged tibial component 48.

Figure 7:
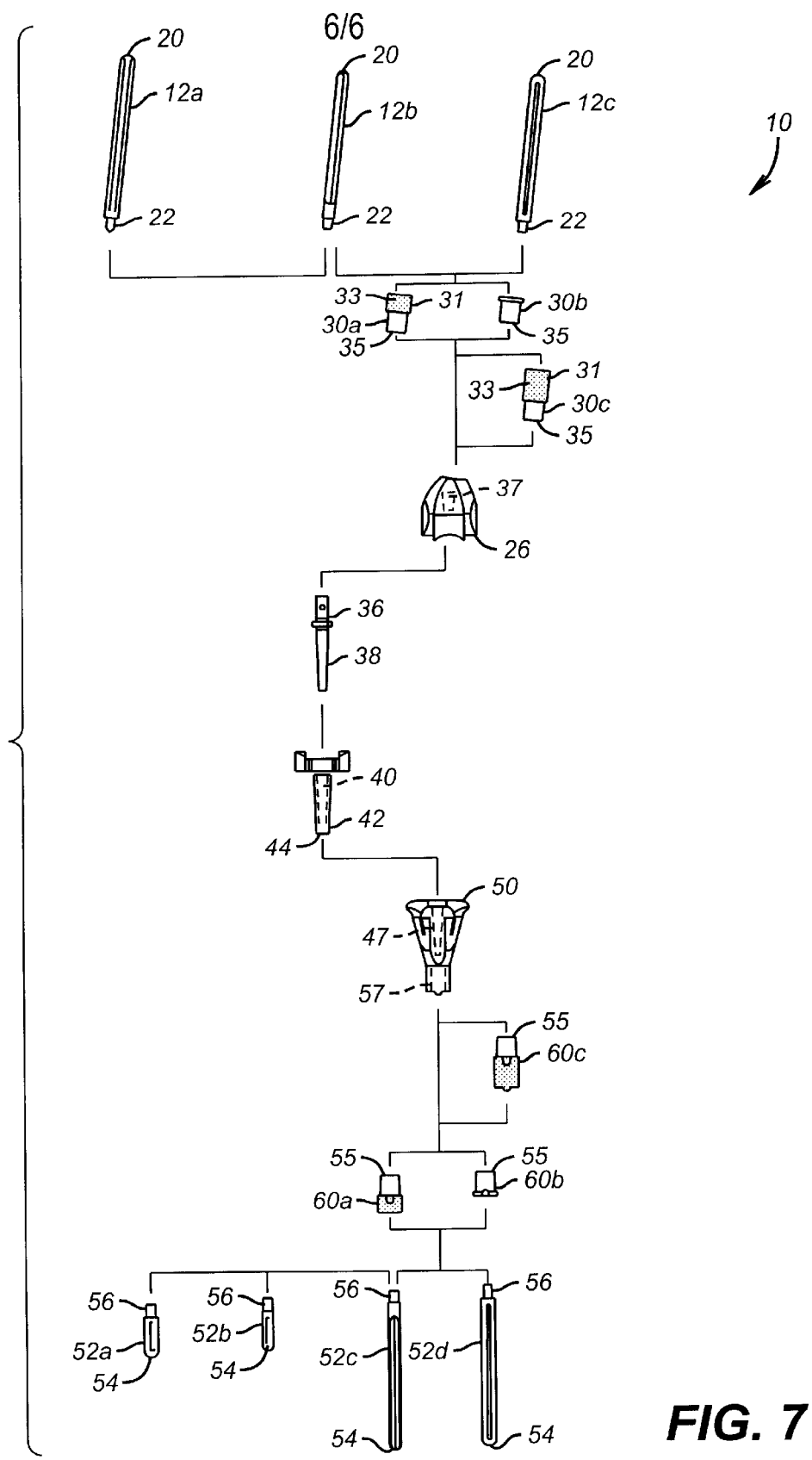
FIG. 7 is a diagrammatic view illustrating another embodiment of a hinged modular knee application.

Another application for the modular system 10 is illustrated in FIG. 7. A selected one of the first stems 12a–c and a selected one of the first adaptors 30a, 30b, may be connected to the distal femoral component 26. A selected one of the second stems 52a–d and a selected one of the second adaptors 60a, 60b, may be connected to the proximal tibial component 50. The distal femoral component 26 may be interconnected with the proximal tibial component 50 by means of the hinge component 36 and the tibial insert 42.

As it can be seen, the principal advantages of these embodiments are that modular components are used for several surgical applications including hinged orthopedic, revision hinged orthopedic, orthopedic oncology and orthopedic trauma. By using the same components in several surgical applications the cost of offering the system is reduced. The surgical technique is simplified because there are fewer instruments required, e.g. implant trials and surgical instruments, because the same technique and instruments can be used for several orthopedic applications. The system is also provided to maintain the anatomically correct joint line for femur, tibia and patella.

As a result, the same hinge component and tibial insert combination is used in various applications. Also, the same hinged tibial component is used for stemmed and stemless applications. A variety of stems can be used with the hinged femoral and distal femoral components, with the hinged tibial and proximal tibial components, and in other modular knee prosthesis applications and systems. In addition, a variety of stems can be used with a variety of adaptors which may include a porous coating.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A modular knee system comprising:

a hinged femoral component and a distal femoral component;

a plurality of first stem components each having a distal tapered male end, the first stem components being selectively compatible with the hinged femoral component;

a plurality of first adaptors, "wherein each adaptor has two tapers of different sizes, the two tapers of different sizes being selectively compatible with the first stem components and the distal femoral component";

a hinge component connected to a tibial insert, the hinge component and tibial insert being selectively compatible with the hinged femoral component and the distal femoral component;

a hinged tibial component and a proximal tibial component selectively compatible with the tibial insert;

a plurality of second stem components each having a proximal tapered male end, the second stem components being selectively compatible with the hinged tibial component; and a plurality of second adaptors, "wherein each adaptor has two tapers of different sizes, the two tapers of different sizes being selectively compatible with the second stem components and the proximal tibial component".

2. The system as defined in claim 1 further comprising a femoral spacer mounted on a surface of the hinged femoral component.

3. The system as defined in claim 1 further comprising a tibial spacer mounted on a surface of the hinged tibial component.

4. The system as defined in claim 1 wherein one of the first and second stem components is a stem having an outer surface including a plurality of flutes extending outwardly therefrom.

5. The system as defined in claim 1 wherein one of the first and second stem components is a stem having an outer surface including a plurality of grooves extending inwardly therefrom.

6. The system as defined in claim 1 wherein one of the first and second adaptors includes an extension portion.

7. The system as defined in claim 6 wherein the extension portion includes a porous annular surface.

8. The system as defined in claim 6 further comprising: a segment connected to one of the adaptors.

9. A modular knee system comprising:

a hinged femoral component and a distal femoral component;

a plurality of first stem components each having a distal tapered male end, the first stem components being selectively compatible with the hinged femoral component;

a plurality of first adaptors wherein each adaptor has a tapered male end of a different size than a distal tapered male end of a selectively compatible first stem component;

a hinge component connected to a tibial insert, the hinge component and tibial insert being selectively compatible with the hinged femoral component and the distal femoral component;

a hinged tibial component and a proximal tibial component selectively compatible with the tibial insert;

a plurality of second stem components and a plug component, the second stem components being selectively compatible with the hinged tibial component, and alternately, the plug component being compatible with the hinged tibial component; and a plurality of second adaptors, the second adaptors being selectively compatible with the second stem components and the proximal tibial component.

10. The system as defined in claim 9 further comprising a femoral spacer mounted on a surface of the hinged femoral component.

11. The system as defined in claim 9 further comprising a tibial spacer mounted on a surface of the hinged tibial component.

12. The system as defined in claim 9 wherein one of the first and second stem components is a stem having an outer surface including a plurality of flutes extending outwardly therefrom.

13. The system as defined in claim 9 wherein one of the first and second stem components is a stem having an outer surface including a plurality of grooves extending inwardly therefrom.

14. The system as defined in claim 9 wherein one of the first and second adaptors includes an extension portion.

15. The system as defined in claim 14 wherein the extension portion includes a porous annular surface.

16. The system as defined in claim 14 further comprising: a segment connected to one of the adaptors.

17. A method of constructing a knee prosthesis comprising:

providing a hinged femoral component and a distal femoral component;

providing a plurality of first stem components each having a distal tapered male end, the first stem components being compatible with the hinged femoral component;

selecting one of the first stern components;

providing a plurality of first adaptors, wherein each adaptor has a tapered male end of a different size than a distal tapered male end of a selectively compatible first stem component;

selecting one of the femoral components;

in response to selecting the hinged femoral component, connecting the selected first stem component to the hinged femoral component;

selecting one of the first adaptors;

alternately, in response to selecting the distal femoral component, connecting the selected first adaptor to the selected first stem component and the distal femoral component;

providing a hinge component connected to a tibial insert;

connecting the selected femoral component with the hinge component and the tibial insert;

providing a hinged tibial component and a proximal tibial component;

providing a plurality of second stem components each having a proximal tapered male end, the second stem components being compatible with the hinged tibial component;

selecting one of the second stem components;

providing a plurality of second adaptors, the second adaptors having two tapers of different sizes with the tapers being compatible with the second stem components and the proximal tibial component;

selecting one of the tibial components;

in response to selecting the hinged tibial component, connecting the selected second stem component to the hinged tibial component;

selecting one of the second adaptors; and alternately, in response to selecting the proximal tibial component, connecting the selected second adaptor to the proximal tibial component.

18. The method as defined in claim 17 further comprising: alternately to the second stem components, providing a plug component and connecting the plug component to the hinged tibial component.

19. The method as defined in claim 17 further comprising:

providing a femoral spacer; and mounting the femoral spacer on a surface of the hinged femoral component.

20. The method as defined in claim 17 further comprising:

providing a tibial spacer; and mounting the tibial spacer on a surface of the hinged tibial component.

21. The method as defined in claim 17 further comprising:

providing an extension portion on one of the first and second adaptors.

22. The method as defined in claim 21 further comprising:

providing a porous annular surface on the extension portion.

* * * * *